United States Patent
Mantz

(10) Patent No.: US 7,362,453 B2
(45) Date of Patent: Apr. 22, 2008

(54) METHOD FOR THE CHARACTERIZATION OF A FILM

(75) Inventor: Ulrich Mantz, Dresden (DE)

(73) Assignee: Infineon Technologies AG, Munich (DE)

( * ) Notice: Subject to any disclaimer, the term of this patent is extended or adjusted under 35 U.S.C. 154(b) by 350 days.

(21) Appl. No.: 10/952,373

(22) Filed: Sep. 29, 2004

(65) Prior Publication Data

US 2005/0095731 A1    May 5, 2005

(30) Foreign Application Priority Data

Sep. 30, 2003  (DE)  ................. 103 45 551

(51) Int. Cl.
*G01B 11/28* (2006.01)

(52) U.S. Cl. .................................... 356/630

(58) Field of Classification Search ........ 356/630–632, 356/503
See application file for complete search history.

(56) References Cited

U.S. PATENT DOCUMENTS

| 5,416,594 A * | 5/1995 | Gross et al. ............. 356/237.5 |
| 5,726,455 A | 3/1998 | Vurens |
| 5,966,312 A | 10/1999 | Chen |
| 6,657,736 B1 * | 12/2003 | Finarov et al. ............. 356/625 |
| 2002/0142498 A1 | 10/2002 | Kubota et al |
| 2002/0183963 A1 | 12/2002 | Kocimski |
| 2002/0197750 A1 | 12/2002 | Tanaka et al. |
| 2004/0021877 A1 * | 2/2004 | Clark ........................ 356/630 |

FOREIGN PATENT DOCUMENTS

DE    199 50 559 A1    5/2001

* cited by examiner

*Primary Examiner*—Tarifur Chowdhury
*Assistant Examiner*—Isiaka O Akanbi
(74) *Attorney, Agent, or Firm*—Patterson & Sheridan, L.L.P.

(57) ABSTRACT

A method for the characterization of a film arranged in a plurality of regions on a substrate forms a respective optical measurement at each of a multiplicity of measurement sites in order to determine a respective measurement result, the measurement result being correlated with a film thickness on the substrate. Measurement results that satisfy a predetermined condition, which is satisfied for a measurement result that has been determined at a measurement site within one of the plurality of regions are selected. The film is characterized on the basis of the selected measurement results.

19 Claims, 2 Drawing Sheets

METHOD FOR THE CHARACTERIZATION OF A FILM

This application claims the benefit of priority to German Application No. 103 45 551.5, which was filed in the German language on Sep. 30, 2003, the contents of which are hereby incorporated by reference.

TECHNICAL FIELD OF THE INVENTION

The present invention relates to a method for the characterization of a film, and in particular, to a method for the characterization of a film arranged in a plurality of regions on a substrate.

BACKGROUND OF THE INVENTION

In numerous areas of technology, films are produced on a wide variety of substrates, the thickness of the films and further parameters being monitored at least in the manner of spot checks in order to regulate the production process in the films or to control subsequent process steps, for example a lateral patterning. The production of a thin semiconductor film on a semiconductor substrate shall be mentioned as an example. The thin semiconductor film is subsequently patterned laterally in order for example to produce a microelectronic or micromechanical component therein. In many cases, thin semiconductor films are also produced such that they are laterally patterned from the outset. In order to be able to measure and monitor the thickness (and other properties) of a thin semiconductor film whose lateral structures have sizes down to a few 10 nm, film thickness analysis areas (FTA sites) are generally provided in semiconductor structures. A film thickness analysis area is typically provided at each chip, so that a wafer, generally comprising a few hundred chips, has a corresponding number of film thickness analysis areas.

In order to measure the film thickness of the semiconductor film, the wafer is firstly oriented roughly on the basis of its groove or notch or cutout and fitted on a table. Afterward, one or more images of the patterned surface of the wafer or of partial regions thereof are recorded and processed by an image or pattern recognition program. The results of the image recognition are subsequently used for a fine adjustment or an exact orientation of the wafer. A measuring instrument then moves to the known sites of the film thickness analysis areas individually. A measured value of the film thickness of the thin semiconductor film is determined at each film thickness analysis area. This is generally done optically, in particular reflectometrically or else ellipsometrically. Once a measured value of the film thickness of the thin semiconductor film has been determined in this way from each film thickness analysis area, the film thickness determined over the wafer, its variation or else systematic variations over the wafer can be calculated in order to characterize the thin semiconductor film on the substrate.

The conventional method described is very time-consuming. In particular, the pattern recognition at the image or images of the wafer surface that is required prior to the fine adjustment of the wafer is computationally intensive and makes a considerable contribution to the fact that the characterization of a film on a wafer takes a long time in the conventional manner. What is particularly disadvantageous in this case is that the wafer has to remain at the measuring device throughout the period of time of the procedure, which may be several minutes long. The throughput of such a conventional measuring device for film thickness analysis is therefore low. Consequently, only a small proportion of all wafers, for example one from each batch, is measured. The conventional method described thus enables only an incomplete monitoring of the film thickness in conjunction with high operating costs (cost of ownership).

A further disadvantage of the conventional method described is that, for each new layout of a wafer, it is necessary to create a new recipe or a new sequential program for the measurement method described. This sequential program has to define, in particular for each new layout, the arrangement of the individual chips, (size, periodicity) on the wafer and the film thickness analysis areas on the individual chip. Furthermore, the image recognition program or the pattern recognition has to be trained to the new layout. In the case of reflectometric or ellipsometric measurements using a film construction model, it is furthermore necessary for the model to be correspondingly changed or adapted each time the film construction is changed. The described changes in the recipe or sequential program in the case of changes to the layout are time-consuming and cost-intensive. They have more of a disadvantageous effect the smaller the number of wafers produced or chips produced. The recipe creation and adaptation and the costs thereof become all the more serious cost factors as the trend leads to production of an ever greater diversity of products within a factory and to ever more rapid renewal or alteration of products and technologies used.

As alternatives to the above-described measuring devices in which, after a fine adjustment of the wafer, in a targeted manner exclusively the film thickness analysis areas are moved to and measured individually, systems already exist in which the entire wafer is scanned or measurements are effected at a multiplicity of measurement points distributed over the entire wafer, from the results of which measurements it is possible to determine the film thickness. So-called scanners scan the entire wafer surface reflectometrically along a regular grid or a periodic lattice.

In another system, the entire wafer surface is detected in a spatially resolved manner by means of a CCD (CCD=charge coupled (optoelectronic) device) and by means of a plurality of wavelength-selective filters optically connected upstream, spectral information also being obtained by means of the filters.

Both systems operate reflectometrically in order to obtain the film thickness from the wavelength dependence of the reflectivity of the surface of the wafer by using a model for the film on the wafer. However, similarly to the measurement method described in the introduction, both systems require knowledge of the size and arrangement of the chips on the wafer and the size and arrangement of the film thickness analysis areas on the chips. These parameters are necessary as input variables in order to select, from the total set of measurement results obtained on the entire wafer, those which have been obtained at film thickness analysis areas. Consequently, these two systems also have to be newly adapted to every new layout of a chip or a wafer.

SUMMARY OF THE INVENTION

The present invention provides an improved method for the characterization of a film arranged in a plurality of regions on a substrate.

In one embodiment of the present invention, there is a method for the characterization of a film arranged in a plurality of regions on a substrate, in which a respective optical measurement is performed at each of a multiplicity of measurement sites on the substrate in order to determine a respective measurement result. Each measurement result is correlated with a film thickness on the substrate. This means, in particular, that if a measurement site lies within one of the plurality of regions in which the film is arranged, the measurement result is a function of the film thickness of the film. If a measurement site lies outside the regions of the plurality of regions, no film or a different film that differs at least in the material or in the thickness is generally arranged there. For these measurement sites, the measurement result is then either a function of the film thickness of the different film or else it is not correlated or weakly correlated with a property of a film present there. This last is the case, for example, if the measurement result is determined by using a model that models the film arranged in the plurality of regions but not the different film arranged outside the plurality of regions.

Measurement results which satisfy a predetermined condition are then selected from the multiplicity of measurement results determined at in each case one of the multiplicity of measurement sites. The predetermined condition is chosen or defined such that it is satisfied for a measurement result that has been determined at a measurement site within one of the plurality of regions. Preferably, the condition is furthermore predetermined or defined such that it is not satisfied, or is satisfied with a lower and preferably with a significantly lower probability, for measurement results that have been determined at measurement sites outside the plurality of regions. The film is subsequently characterized on the basis of the selected measurement results.

A measurement result comprises a directly or indirectly determined measured value of the film thickness or one or a plurality of measured values that are a function of the film thickness, for example reflectivities at one or a plurality of different wavelengths and in the case of one or a plurality of different planes of polarization of the incident light or reflected light. As an alternative, a measurement result furthermore comprises further parameters that can be determined directly or indirectly from the measurement. In the case of using a model for the film of the film structure, this is for example the goodness of fit (GOF) or another similarity parameter that is a measure of the maximum achievable correspondence or similarity between the measurement data detected empirically and simulated with the aid of the parameter-dependent model.

In accordance with a preferred exemplary embodiment, the predetermined condition is that the similarity parameter has a (generally maximum or minimum) value corresponding to a maximum similarity or a value in a corresponding (narrow) predetermined similarity parameter interval or satisfies another suitable predetermined similarity parameter condition.

As an alternative or in addition, a measured value distribution function is calculated from the measured values or from the measured values whose assigned similarity parameter satisfies the predetermined similarity parameter condition. In this case, the predetermined condition preferably comprises the condition that the measured value lies within a measured value interval within which the measured value distribution function has a maximum with a predetermined property. In other words, a measured value interval is sought within which the measured value distribution function has a maximum with a predetermined minimum height, a width within a predetermined width interval, a ratio between height and width within a predetermined interval or another predetermined property. Preferably, the maximum is sought within a predetermined vicinity around an expected measured value.

Furthermore, it is preferably the case in the method according to the invention that, for each measurement result that satisfies the predetermined condition, the measurement site at which the measurement result was determined is determined. The film is then preferably characterized on the basis of those selected measurement results whose measurement sites are furthermore arranged in a regular grid. This method can advantageously be used whenever the substrate examined is laterally periodically patterned or the structures are arranged on the substrate regularly in grid-type fashion.

Besides determining a mean value of the film thickness, the characterization of the film preferably comprises further statistical parameters, for example a variant or a dispersion, which describe the distribution function of the film thicknesses within the plurality of regions. As an alternative or in addition, the characterization furthermore comprises the determination of systematic variations in the film thickness over the wafer, for example an increase or decrease in the film thickness from the center to the edge or from one side of the wafer to the other.

The method is preferably applied to film thickness analysis areas that are generally laterally unpatterned and are arranged in a relatively high number periodically on the wafer. As an alternative, the method according to the invention is applied to an arbitrarily patterned wafer without areas specifically provided for a film thickness analysis. This is possible if the wafer has other regions with the film to be characterized and the measurement sites or measurement spots are preferably so small that they lie fully within the regions at least statistically given a sufficient number of regions. The method according to the invention automatically identifies those measurement results that have been determined at measurement sites lying within the regions in which the film is arranged.

One advantage of the present invention in the exemplary embodiments is that it does not require image or pattern recognition and orientation and fine adjustment of the wafer. As a result, the overall duration during which a wafer stays in a measuring device is drastically reduces and the throughput of the measuring device is correspondingly increased. Therefore, with a same number of measuring devices, it is possible to measure a significantly greater number of wafers. In particular, the present invention enables the continuous detection or measurement of the wafers in a production line. Thus, for the same or even lower operating costs, the present invention provides a significantly higher safeguarding with respect to parameter deviations in a production line. In this case, the present invention is based on the fact that the wafers are completely scanned or measured by means of a simple and therefore very fast method and the measurement results thus obtained are subsequently evaluated, or obtained from measurement data, "offline" at a time at which the measuring instrument is already detecting one or a plurality of further wafers.

Since the method according to the invention preferably scans the entire wafer, in particular regions in which the film is arranged, for example film thickness analysis areas, are measured. This results in optimum statistics for a characterization of the film and its variability from the measured values. This in turn enables an accurate, reliable and complete detection of fluctuations or deviations of production parameters from desired values.

BRIEF DESCRIPTION OF THE DRAWINGS

Exemplary embodiments of the present invention are explained in more detail below with reference to the accompanying figures, in which.

DETAILED DESCRIPTION OF THE INVENTION

Figure 1:
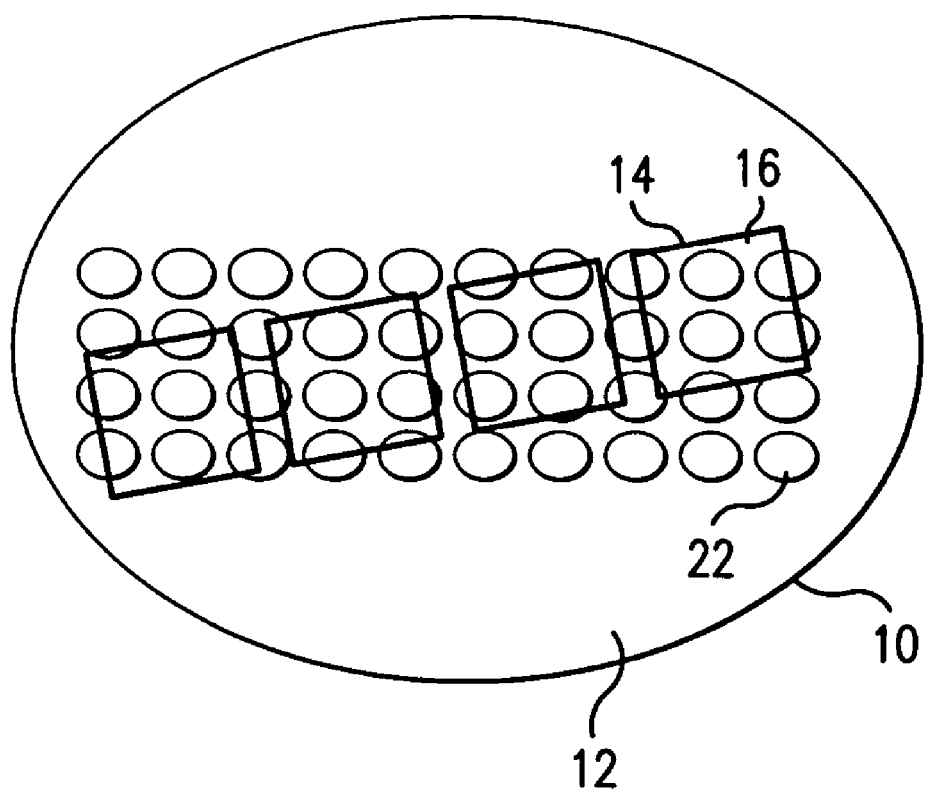
FIG. 1 shows a plan view of a wafer according to the invention.

FIG. 1 is a diagrammatic illustration, not to scale of a plan view of a substrate 10, for example a semiconductor wafer. A plurality of regions 14 each square in the illustration are arranged on a surface 12 of the substrate 10, in which regions a film 16 is arranged on the surface 12 of the substrate 10. The regions 14 are for example film thickness analysis areas within which the film 16 is laterally unpatterned. The film thickness analysis areas are generally provided in a multiplicity or at least in a plurality on a wafer. A film thickness analysis area is typically provided on each chip, so that a wafer with a few hundred chips has a corresponding number of film thickness analysis areas.

The film 16 is generally also present outside the film thickness analysis areas on the surface 12 of the wafer 10, but is laterally patterned there and, in this form, is part of a microelectronic or micromechanical component or of some other functional structure. Typical feature sizes nowadays are a few tens of nm. It is not possible, however, to determine a film thickness optically within a laterally unpatterned area having a linear extent of a few tens of nm. This is primarily due to the fact that the wavelengths of the light used from the infrared, the visible region or else the near ultraviolet are greater or significantly greater than said feature sizes. In order still to be able to characterize or measure a film and in particular its film thickness even when it has already been laterally patterned with the feature size described, or has even been laterally patterned from the outset, the film thickness analysis areas are provided, which have a linear dimension of typically approximately 100 μm, and within which the film is laterally unpatterned. Within an area of this size, it is readily possible to determine the film thickness optically, in particular for example reflectometrically or ellipsometrically.

A real wafer may deviate from the illustration in FIG. 1 inter alia insofar as FIG. 1 shows a plurality of film thickness analysis areas or regions 14 which are arranged closely adjacent to one another and together occupy a not inconsiderable proportion of the surface 12 of the substrate 10. In actual fact, the film thickness analysis areas generally have a lowest possible proportion of area on the surface 12 of the substrate 10 since they generally do not have any further functions and in particular have no function for a finished, functional chip.

The present invention provides for a respective optical measurement to be performed at each of a multiplicity of measurement sites 22. As illustrated in FIG. 1, the measurement sites 22 are preferably arranged periodically in a regular grid or two-dimensionally. The multiplicity of measurement spots or measurement sites 22 is preferably arranged such that even in the case of a roughly adjusted orientation of the wafer 10 or else in the case of a totally unknown orientation of the wafer 10 and thus absolute locations of the film thickness analysis areas or regions 14 that are unknown in the system of coordinates of the measuring device, at least one measurement site 22 is in each case located in each region or at least in a number of regions 14 that suffices for the given purpose and the required measurement accuracy.

FIG. 1 illustrates the situation where the wafer 10 has a plurality of regions 14 arranged along a straight line. Since the approximate orientation of the wafer 10 and thus the approximate locations of the regions 14 are known, the measurement sites 22 are arranged two-dimensionally periodically within a rectangle whose side lengths and whose location on the wafer are chosen such that at least one measurement site 22 is located within each individual one of the regions 14 in a definite fashion or at least with a sufficiently high probability.

The arrangement of the measurement sites 22 illustrated in FIG. 1 can also advantageously be used when instead of a linear arrangement of the regions 14, a two-dimensional lattice-type arrangement of the regions 14 is present but only one or a few rows of the regions 14 are to be scanned. Accordingly, the arrangement and distribution of the multiplicity of measurement sites 22 can be varied within wide limits and can be adapted to the wafer layout, in particular the arrangement of the film thickness analysis areas or other regions 14 to be detected, and to the requirements. The greatest quantity of information and thus the most precisely and most reliable characterization of the film are obtained if all the regions 14 present on the wafer 10 are scanned or at least one measurement site 22 is located within each region 14. In the practical general case of a two-dimensionally periodic arrangement of film thickness analysis areas distributed essentially over the entire wafer, the measurement sites 22 are preferably arranged in a two-dimensionally periodic structure that likewise extends essentially over the entire wafer.

The size of the individual measurement spots or measurement sites 22 is preferably chosen such that at least one measurement site 22 lies in each region 14 in a definite fashion or at least with a sufficient probability, said measurement site being arranged completely within the measurement region 14. This ensures that the measurement result determined at said measurement site is influenced exclusively by the film present in the regions 14, and not also by other films present outside the regions 14. This condition is satisfied if the linear dimension of each measurement spot 22 in every direction is at least half as large as the corresponding dimension of a region 14.

In accordance with a preferred exemplary embodiment, a reflectivity spectrum is detected reflectometrically at each measurement site. Measurement data representing the reflectivity of the wafer 10 or its surface 12 for one wavelength, preferably for a plurality of wavelengths are obtained. A model with a free parameter is determined for the film 16 arranged in the regions 14, the free parameter mapping the film thickness of the film 16. Corresponding model measurement data are simulated or calculated for the model. Said model measurement data are generally dependent on the free parameter. By varying the free parameter, the model measurement data are fitted or adapted to the empirically detected measurement data. The measurement result is determined from that value of the free parameter for which the detected measurement data and the model measurement data have a maximum similarity. This measurement result comprises that value of the free parameter for which the detected measurement data and the model measurement data have a maximum similarity, as measured value of the film thickness.

When the model measurement data are fitted to the detected measurement data, use is made of a similarity parameter that is a measure of the similarity between the model measurement data and the detected measurement data. This involves a correlation factor, for example the so-called goodness of fit (GOF), or an equivalent parameter. The similarity parameter is generally defined such that it has a value all the larger or all the smaller the better the correspondence between the model measurement data and the detected measurement data. In the idealized limiting case of perfect correspondence between the model measurement data and the detected measurement data, the similarity parameter then has a maximum value (for example 1) or a minimum value (for example 0). The value of the similarity parameter that represents the degree of similarity or correspondence or correlation between the model measurement data for that value of the free parameter for which the detected measurement data and the model measurement data have a maximum similarity and the detected measurement data is likewise part of the measurement result. The further steps of the method are illustrated below with reference to FIGS. 2 and 3.

Figure 2:
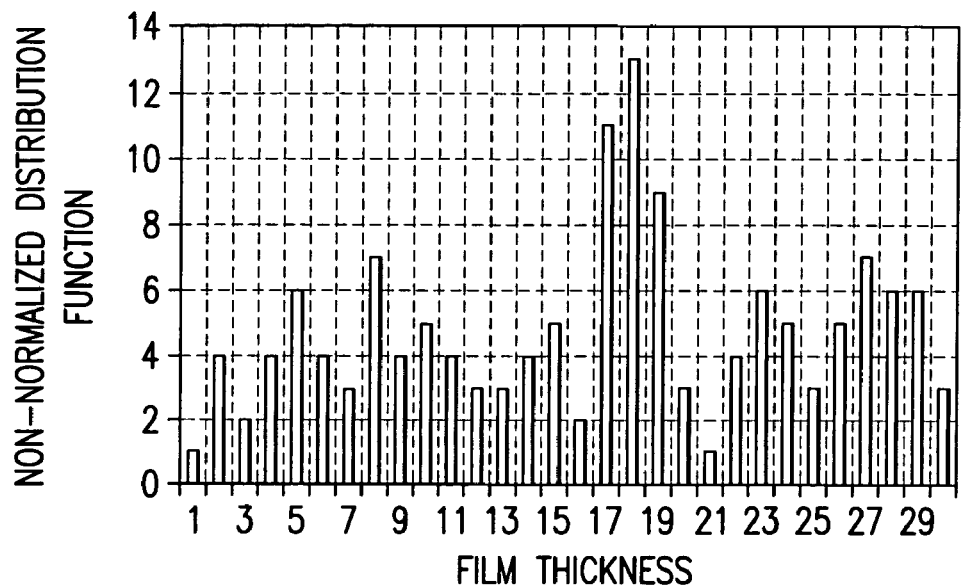
FIG. 2 shows a first distribution function used in according to the invention.

FIG. 2 is a diagrammatic illustration of the distribution of the film thickness measured values from all the measurement sites in the form of a histogram. The abscissa is assigned the film thickness in arbitrary units, for example in nm. The ordinate illustrates the non-normalized distribution function or the number of measured values within the film thickness intervals illustrated. The distribution of 286 measured values illustrated in FIG. 2 has the function of an example and was not taken from real measurements. The number of measured values is significantly higher for a real wafer. It is approximately 12.5 million for example for a wafer having a diameter of 200 mm and measurement sites arranged in the form of a square lattice with a period of 50 μm. Accordingly, a real distribution function is generally smoother than that illustrated in FIG. 2.

The measurement results illustrated in FIG. 2 originate both from measurement sites 22 lying within one of the plurality of regions 14 and from such measurement sites which lie outside the regions 14. The above-described model models the film arranged within the regions 14. Accordingly, for measurement sites lying within one of the regions 14 and thus on or in the film, it is possible to obtain, for a specific value of the free parameter, a good or very good correspondence between the model measurement data and the detected measurement data. Accordingly, the measurement result at a measurement site in one of the regions 14 comprises a measured value precisely defined by the fit and a similarity parameter that represents or indicates a good or very good correspondence between the model measurement data and the detected measurement data.

At measurement sites lying outside the regions 14, generally no film at all is present or a different film than the film arranged in the regions 14 is present, or, although the same film is present, it is laterally patterned and thus not homogeneous within the measurement spot. This generally has the effect that it is not possible to obtain a good correspondence between the model measurement data and the detected measurement data. This also usually has the consequence that the measured value of the film thickness is defined relatively poorly as the optimum value of the free parameter and varies to a disproportionately great extent given very small variations of the properties of the substrate within the measurement spot. A measurement result from a measurement site 22 outside the regions 14 therefore generally comprises a similarity parameter that indicates a poor correspondence between the model measurement data and the detected measurement data, and a measured value that is defined relatively poorly.

Consequently, there are a plurality of criteria which can be taken as a basis for determining whether a measured value originates from a measurement site 22 within or outside the regions 14. These criteria may be applied individually, but a plurality of the criteria mentioned hereinafter are preferably combined with one another or applied simultaneously in order to reliably discriminate both groups of measured values.

As already mentioned, a measured value from a measurement site within one of the regions 14 is defined relatively well by the good correspondence that can be achieved between the simulated model measurement data and the empirically detected measurement data. Therefore, the measured values from the regions 14 lie within a small range of film thicknesses, where they form a narrow or sharp peak or a narrow or sharp maximum. If no undesired deviation of process parameters has occurred during the production of the film, said maximum furthermore lies in proximity to the desired value or the nominal film thickness.

Such a maximum is discernible in the case of the film thickness 18 in FIG. 2. It can be identified for example on the basis of a predetermined minimum height, on the basis of a width lying within a predetermined width interval, on the basis of an area lying within a predetermined area interval, on the basis of a ratio between two of the parameters mentioned that lies within a predetermined interval, on the basis of a position of the maximum within a predetermined vicinity of an expected measured value, or on the basis of another predetermined property. The area of the maximum or the area below the maximum should for example approximately correspond to the product of the number of regions 14 and the average number of measurement sites 22 lying within a region 14. The width of the maximum is determined by the measurement error and by the variability of the film thickness over the wafer 10. Therefore, a predetermined maximum width of the maximum can be expected for a wafer having a specific lateral homogeneity of the film thickness of the film and for a measuring device with a known measurement inaccuracy.

Figure 3:
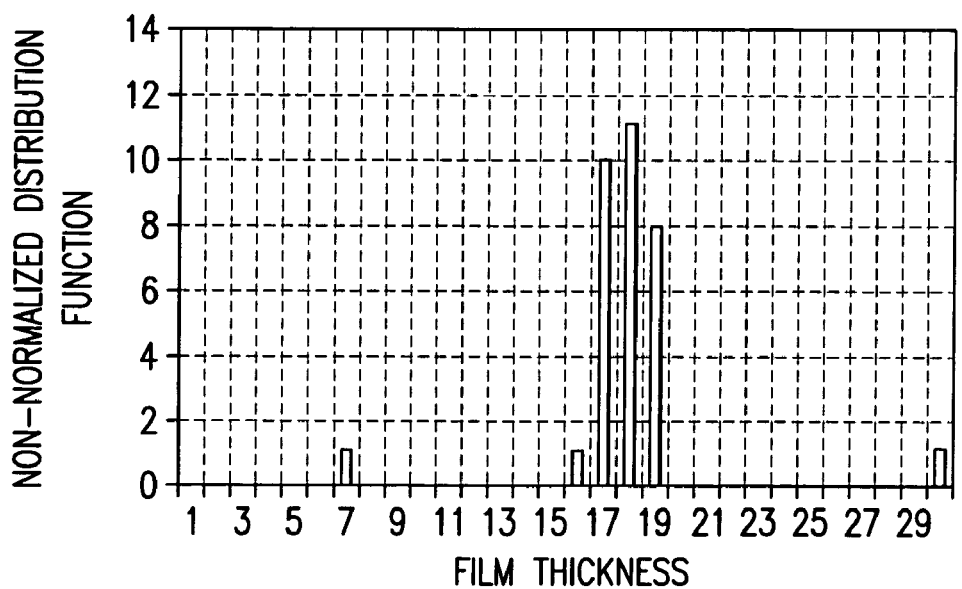
FIG. 3 shows a second distribution function used according to the invention.

A further criterion on the basis of which measurement results from the regions 14 can be distinguished from other measurement results is the value of the similarity parameter. FIG. 3 is a diagrammatic illustration of a diagram which corresponds to that illustrated in FIG. 2 but which illustrates or takes into consideration those 32 measured values whose assigned similarity parameters indicate a great similarity between the simulated model measurement data and the empirically detected measurement data. Most of the measured values from the peak between the film thicknesses 17 and 19 originate from measurement sites from the regions 14 for which the similarity parameter indicates a good correspondence. Measured values lying outside said peak generally originate from measurement sites lying completely or at least partly outside the regions 14. Therefore, the assigned similarity parameter generally indicates a poor correspondence between the model measurement data and the empirically detected measurement data. If only the measured values whose similarity parameter indicates a good correspondence are taken into consideration, almost all that remain are measured values within the film thickness interval 17 to 19.

FIG. 3 reveals that, however, a similarity parameter that indicates a good correspondence is also assigned to individual measured values outside the peak, to be precise in the case of the film thicknesses 7, 16 and 30. Furthermore, comparison of FIGS. 2 and 3 reveals that even within the film thickness interval 17 to 19 there are a few measured values whose assigned similarity parameters indicate a poor correspondence, and which therefore with high probability originate from measurement sites 22 outside the regions 14. These are random results, the number of which is determined inter alia by the performance of the model chosen or by its closeness to reality and by the set of empirically detected measurement data and measurement data simulated on the basis of the model. The more powerful the model is and the more measurement data are detected at each measurement site, the less frequently a similarity parameter from a measurement site outside the regions 14 indicates a good correspondence, and the less frequently a measured value from a measurement site outside the regions 14 lies within the film thickness interval including the peak. Consequently, a combination of the similarity parameter criterion and the peak criterion affords a good and reliable discrimination between measurement results which originate from measurement sites within the regions 14 and those which originate from other measurement sites.

Thus, in accordance with the preferred exemplary embodiment of the present invention, those measurement results are selected which lie within the measured value interval 17 to 19 within which the measured value distribution function has a maximum having the above-described predetermined property, and whose similarity parameter indicates a good correspondence between the simulated model measurement data and the empirically detected measurement data. In the case of these selected measurement results, it can be assumed with high probability that they originate from measurement sites within the regions 14.

The film is then characterized on the basis of the selected measurement results, this characterization preferably being effected by the mean value of the measured values, which represents the film thickness of the film 16 averaged over the wafer. Preferably, the variance or the standard deviation of the distribution of the measured values within the measured value interval (film thicknesses 17 to 19) or another parameter that maps the variability of the measured values is furthermore calculated for the characterization of the film 16. Further parameters that may serve for characterizing the film are for example those which specify an increase or decrease in the film thickness from the center to the edge of the wafer or along a specific direction or a maximum and a minimum film thickness of the film 16 on the wafer.

In accordance with a preferred embodiment, for each measurement result that satisfies the predetermined condition, the measurement site at which the measurement result was determined is determined. The measurement results from measurement sites arranged in a regular grid are then taken into consideration for the characterization of the film. This further criterion precludes those few measurement results which do not originate from the regions 14 but nevertheless lie randomly within the peak and have a similarity parameter that indicates a good correspondence.

As already mentioned, the fit of the simulated model measurement data to the empirically detected measurement data is all the more accurate and reliable the more measurement data are included in said fit. Preferably, the reflectivity is therefore measured at a largest possible number of wavelengths within a largest possible wavelength range, in the case of two or more different planes of polarization of the incident light or the reflected light, and at a plurality of angles of incidence of the incident light with respect to the surface 12 of the wafer 10. Therefore, ellipsometry can also be used in addition to the reflectometry described in the exemplary embodiment described above. In the sense of optimizing the relationship between the precision and the reliability of the characterization of the film, on the one hand, and the measurement complexity including the computation complexity that occurs during the fitting, on the other hand, and taking account of the available measurement technology, by way of example, the detection of a reflectivity spectrum within a specific wavelength interval in the case of one direction of polarization or in the case of unpolarized light and also at a single angle of incidence will therefore represent an optimum for many applications.

In addition to the modeling described in the exemplary embodiment illustrated above, for merely monitoring production or the film thickness in a current production line, a simple comparison between the measurement data detected at each measurement site and the reference measurement data detected at a reference film on a reference wafer is advantageous on account of the low computing power required.

Conversely, it is also possible to effect an analysis of different models for different films or film stacks for one and the same wafer. For this purpose, the method according to the invention described above is carried out repeatedly for the plurality of different models in order to characterize different films that are present in different groups of film thickness analysis areas.

Preferably, the regions 14, as mentioned above, are areas which are provided for the film thickness analysis and within which the film 16 is laterally unpatterned. As an alternative, the regions 14 are areas which are not patterned for arbitrary reasons, and which are large enough that, with a sufficient probability, a measurement spot 22 lies completely within a region 14 in order to enable a good correlation between the model and the film and thus also a good similarity parameter.

What is claimed is:

1. A method for determining a thickness of a film arranged in a plurality of regions on a substrate, comprising:
performing a respective optical measurement at each of a plurality of measurements sites on the substrate to determine a respective measurement result, measurement sites lying within the plurality of regions and other measurement sites lying outside the plurality of regions, and the measurement result being correlated with a film thickness on the substrate;
selecting measurement results which satisfy a predetermined condition, which is satisfied for a measurement result that has been determined at a measurement site within one of the plurality of regions, and which is satisfied with a lower probability for a measurement result that has been determined at a measurement site outside the plurality of regions; and
determining the thickness of the film based on the selected measurement results, wherein each measurement result comprises a measured value, and the selecting further comprises:
calculation of a measured value distribution function from the measured values,
the predetermined condition comprising the condition that the measured value lies within a measured value interval within which the measured value distribution function has a maximum with a predetermined property.

2. The method as claimed in claim 1, wherein the predetermined property of the maximum is a predetermined minimum height of the maximum or a width of the maximum within a predetermined width interval or an area of the maximum within a predetermined area interval or a position of the maximum within a predetermined vicinity of an expected measured value.

3. The method as claimed in claim 1, wherein the regions of the plurality of regions are arranged regularly in grid-type fashion,
for each measurement result that satisfies the predetermined condition, the measurement site at which the measurement result was determined being determined,
the characterizing taking into consideration measurement results from measurement sites that are arranged in a regular grid.

4. The method as claimed in claim 1, wherein characterizing of the film includes a determination of a variability of the film thickness of the film within the plurality of regions.

5. The method as claimed in claim 1, wherein the film is produced simultaneously or in a same way within the plurality of regions, and in which films that are produced in one or a plurality of other ways or are laterally patterned are arranged in other regions on the substrate.

6. The method as claimed in claim 1, wherein the substrate is a semiconductor substrate.

7. The method as claimed in claim 1, wherein the optical measurement comprises a reflectometric measurement or an ellipsometric measurement.

8. The method as claimed in claim 1, wherein the regions of the plurality of regions are laterally unpatterned film thickness analysis areas.

9. The method as claimed in claim 1, wherein the measurement sites of the multiplicity of measurement sites are arranged in a one- or two-dimensional periodic grid.

10. A method for determining a thickness of a film arranged in a plurality of regions on a substrate, comprising:
performing a respective optical measurement at each of a plurality of measurements sites on the substrate to determine a respective measurement result, measurement sites lying within the plurality of regions and other measurement sites lying outside the plurality of regions, and the measurement result being correlated with a film thickness on the substrate;
selecting measurement results which satisfy a predetermined condition, which is satisfied for a measurement result that has been determined at a measurement site within one of the plurality of regions, and which is satisfied with a lower probability for a measurement result that has been determined at a measurement site outside the plurality of regions;
determining the thickness of the film based on the selected measurement results; and
determining a model of the film with a free parameter that maps the film thickness,
wherein the performing of an optical measurement at each of the plurality of measurement sites comprises:
detecting of measurement data;
simulating corresponding model measurement data for the model depending on the free parameter; and
determining the measurement result from that value of the free parameter for which the detected measurement data and the model measurement data have a maximum similarity.

11. The method as claimed in claim 10, the determining of the measurement result comprises
a determination of a similarity parameter comprising a degree of similarity of the detected measurement data and the model measurement data for that value of the free parameter for which the detected measurement data and the model measurement data have a maximum similarity,
the predetermined condition comprising the similarity parameter satisfying a predetermined similarity parameter condition.

12. The method as claimed in claim 11, wherein the calculating of the distribution function takes into consideration measured values from measurement sites for which the similarity parameter satisfies the predetermined similarity parameter condition.

13. The method as claimed in claim 10, wherein the regions of the plurality of regions are arranged regularly in grid-type fashion,
for each measurement result that satisfies the predetermined condition, the measurement site at which the measurement result was determined being determined,
the characterizing taking into consideration measurement results from measurement sites that are arranged in a regular grid.

14. The method as claimed in claim 10, wherein characterizing of the film includes a determination of a variability of the film thickness of the film within the plurality of regions.

15. The method as claimed in claim 10, wherein the film is produced simultaneously or in a same way within the plurality of regions, and in which films that are produced in one or a plurality of other ways or are laterally patterned are arranged in other regions on the substrate.

16. The method as claimed in claim 10, wherein the substrate is a semiconductor substrate.

17. The method as claimed in claim 10, wherein the optical measurement comprises a reflectometric measurement or an ellipsometric measurement.

18. The method as claimed in claim 10, wherein the regions of the plurality of regions are laterally unpatterned film thickness analysis areas.

19. The method as claimed in claim 10, wherein the measurement sites of the multiplicity of measurement sites are arranged in a one- or two-dimensional periodic grid.

* * * * *